United States Patent
Rehnke

(10) Patent No.: US 9,913,711 B2
(45) Date of Patent: Mar. 13, 2018

(54) INTERNAL LONG TERM ABSORBABLE MATRIX BRASSIERE

(71) Applicant: Robert D. Rehnke, St. Petersburg, FL (US)

(72) Inventor: Robert D. Rehnke, St. Petersburg, FL (US)

( * ) Notice: Subject to any disclaimer, the term of this patent is extended or adjusted under 35 U.S.C. 154(b) by 0 days.

(21) Appl. No.: 14/736,945

(22) Filed: Jun. 11, 2015

(65) Prior Publication Data

US 2017/0224471 A1    Aug. 10, 2017

Related U.S. Application Data

(60) Provisional application No. 62/010,624, filed on Jun. 11, 2014.

(51) Int. Cl.
*A61F 2/12* (2006.01)

(52) U.S. Cl.
CPC ...................... *A61F 2/12* (2013.01)

(58) Field of Classification Search
CPC ........................................ A61F 2/12
USPC ........................................ 623/7–8
See application file for complete search history.

(56) References Cited

U.S. PATENT DOCUMENTS

| | | | |
|---|---|---|---|
| 4,470,160 A * | 9/1984 | Cavon | A61F 2/12 128/DIG. 21 |
| 6,055,989 A | 5/2000 | Rehnke | |
| 6,210,439 B1 | 4/2001 | Firmin et al. | |
| 6,875,233 B1 * | 4/2005 | Turner | A61F 2/12 623/8 |
| 6,902,932 B2 | 6/2005 | Altman et al. | |
| 7,081,135 B2 * | 7/2006 | Smith | A61F 2/12 606/151 |
| 7,998,152 B2 | 8/2011 | Frank | |
| 8,858,629 B2 | 10/2014 | Moses et al. | |
| 9,549,812 B2 * | 1/2017 | Shetty | A61F 2/0059 |
| 2008/0097601 A1 * | 4/2008 | Codori-Hurff | A61F 2/12 623/8 |
| 2008/0300681 A1 | 12/2008 | Rigotti et al. | |
| 2009/0125107 A1 * | 5/2009 | Maxwell | A61F 2/12 623/8 |
| 2009/0234459 A1 * | 9/2009 | Sporring | A61F 2/30721 623/18.11 |
| 2010/0023029 A1 | 1/2010 | Young | |
| 2010/0191330 A1 | 7/2010 | Lauryssen et al. | |
| 2011/0009960 A1 | 1/2011 | Altman et al. | |
| 2011/0224703 A1 | 9/2011 | Mortarino | |
| 2011/0257665 A1 | 10/2011 | Mortarino | |
| 2012/0004723 A1 | 1/2012 | Mortarino et al. | |
| 2012/0010706 A1 * | 1/2012 | Schuessler | A61F 2/12 623/8 |
| 2012/0022646 A1 | 1/2012 | Mortarino et al. | |
| 2012/0029537 A1 | 2/2012 | Mortarino | |
| 2012/0150204 A1 | 6/2012 | Mortarino et al. | |
| 2012/0185041 A1 | 7/2012 | Mortarino et al. | |
| 2012/0221105 A1 | 8/2012 | Altman et al. | |
| 2013/0006279 A1 | 1/2013 | Mortarino | |

(Continued)

FOREIGN PATENT DOCUMENTS

FR    2682284    4/1993

*Primary Examiner* — Suzette J Gherbi

(57) ABSTRACT

A long term absorbable matrix brassiere including a circular tube member adapted to be fixed to the chest of a woman, a membrane or tarpaulin fixed within the tube member; and a cup held within the tube member.

6 Claims, 9 Drawing Sheets

(56) References Cited

U.S. PATENT DOCUMENTS

| | | |
|---|---|---|
| 2013/0103149 A1 | 4/2013 | Altman et al. |
| 2013/0253645 A1 | 9/2013 | Kerr et al. |
| 2013/0304098 A1 | 11/2013 | Mortarino |
| 2014/0081076 A1* | 3/2014 | Schutt ................ A61B 17/0401 600/31 |
| 2014/0088700 A1 | 3/2014 | Mortarino et al. |
| 2014/0222146 A1 | 8/2014 | Moses et al. |
| 2014/0277000 A1 | 9/2014 | Mortarino et al. |
| 2015/0112434 A1* | 4/2015 | Felix ...................... B29C 47/08 623/8 |
| 2015/0223928 A1* | 8/2015 | Limem .................... A61F 2/12 623/8 |
| 2016/0022416 A1* | 1/2016 | Felix ...................... B29C 47/08 623/8 |

* cited by examiner

INTERNAL LONG TERM ABSORBABLE MATRIX BRASSIERE

CROSS-REFERENCE TO RELATED PATENT APPLICATION

This application claims priority from U.S. provisional patent application Ser. No. 62/010,624 filed Jun. 11, 2014, the entire disclosure of which is incorporated herein by reference.

BACKGROUND OF THE INVENTION

Field of the Invention

The present invention pertains generally to a device for surgical correction and prevention of breast ptosis and acts as an internal long term absorbable matrix brassiere. More particularly, the invention constitutes a device, made of available long term absorbable matrices, that repairs or re-enforces the anatomy of the breast and is responsible for its shape and anchorage to the chest wall via the circum-mammary ligament.

Brief Discussion of the Related Art

Brassieres had their origin in the 19th century and were preceded by the corset, which was fabricated in one piece with ribbing as supports, originally made of whalebone then metal, to push the breast up and squeeze the waistline in. The origins of similar articles of fashion dates back 3,000 years to the Minoan civilization, whose Snake Goddess wore a corset like device which pushed the breasts up and together, exposing them in an uncovered central position. The succeeding Mycenaeans continued the tradition, as the breast held special cultural and religious significance to them. These undergarments have always had roots dually in fashion and the more practical supportive health concerns. They have been an expression of female beauty and social hierarchy.

One hundred years ago, Mary Phelps Jacob (after marriage known as Caresse Crosby), obtained a patent from the US patent office for a backless brassiere she made from two handkerchiefs. Legend has it that Mary, who was a 19 year old member of New York City society, had to create an alternative to a corset when planning her ensemble for the debutant ball. She and her maid attached two handkerchiefs together with pink ribbon and a cord. The fashion was such a success that her friends commissioned more made for themselves. Realizing she had invented something useful, Mary went on to submit a patent for a "Backless Brassier", which was granted in November of 1914. Years later she would sell this intellectual property to Warners Brothers Corset Company, of Bridgeport, Conn.

Plastic Surgery figured prominently in the story of youthful, full, and lifted breast, when the breast implant was introduced in the 1960's. Thomas Cronin and Frank Gerow collaborated with Dow Corning in 1961 to develop the first silicone breast implant. Shortly after, in 1962 the first breast augmentation with a silicone implant was performed. The rest, as they say, is history; over 300,000 breast implant surgeries are performed each year.

The anatomy of the breast and chest has a great deal to do with the shape and perkiness of the breast, something both bras and implants are trying to influence. The breast, an organ consisting of both glandular tissue and fat, is shaped by collagen connective tissue, called fascia that anchors and supports the breast to the underlying chest wall. Sir Astly Cooper, in the 19th century, described the two layers of superficial fascia that surround the breast and anchor it to the chest wall. He described the connective tissue extensions, named after him (Coopers ligaments) which run from this superficial fascia up to the under surface of the skin to anchor the skin to the breast. It has been felt that when Coopers ligaments stretch out, the breasts then sag. However, what has not been appreciated until now is the exact nature of how the superficial fascia attaches to the chest—the circum-mammary ligament. This fascia, like a corral, is called the circum-mammary ligament, which defines the perimeter of the breast. In addition it fuses to the fascia covering the chest wall and anchors it in place. The most defined aspect of this structure is located under the breast, called the infra-mammary fold ligament. The next most developed is the medial, or inner aspect of the corral. This inner portion of the circum-mammary ligament causes the separation between the breasts and is responsible for the cleavage. Laterally, towards the outer portion of the breast, the cir-cum-mammary ligament is not as strong or well defined. It is this portion of the suspensory ligament of the breast that is most responsible for sagging, or ptosis, of the breast. As was previously mentioned, the breast sits upon the chest wall which is its foundation. The foundation has a great deal of impact on the shape and projection of the breast. Most human anatomy is not perfectly geometric or symmetric. Thus there are usually differences in the boney rib cage on the left and right that lead to asymmetry of the breasts. With a person lying on their back, or as anatomist say the supine position, the rib cage is like a flattened cylinder—that is wider than it is tall. Also, as one travels from the center point of the chest, or sternum, towards the outer or lateral aspect, the flat portion of the chest must slope downward. As one moves out from the center and around the chest, it becomes more cylindrical as it turns to the back, which once again is flattened. The portion of the breast located on the downward slope of the lateral chest wall, effects how it is pulled down by gravity in the supine position, or pressed away from the center of the chest in the prone position (like the keel of a boat pushing through water). So it is true that gravity pulls the breast down but this happens because the inherent anatomy (weaker attachment of the circum-mammary ligament to the chest and a sloping chest wall laterally) and its effect in the prone and supine position. A flatter, more rectangular chest supports the breast position more than a more rounded, cylindrical chest which leaves the breast attached to the side of the chest without an underlying foundation. Since the human form is asymmetric, one can have less support from the chest on one side, than on the other, resulting in more sagging, or ptosis, on that side. The larger the breast, the more the stretching force. The presence of breast implants can greatly exacerbate this situation.

Ironically, plastic surgery involving breast implants frequently weakens the body's natural, internal bra—the superficial fascia system and circum-mammary ligament. Even more destructive to the shape of the breast is mastectomy for breast cancer. Despite modern skin and nipple sparing procedures, having been accepted as cutting edge cancer care, most surgeons are insufficiently knowledgeable or skilled to save the circum-mammary ligament, and take full advantage of this minimally invasive approach to mastectomy.

Therefore many woman, with large heavy breast or women who have had breast surgery, end up with weakened supporting structures of the breast and suffer breast sagging. The original breast lift and reduction technique was developed by plastic surgeon Robert J. Wise. It used a "key hole" skin reduction pattern that left an anchor shaped scar on the breast. A technique which followed, by LeJour, omitted the horizontal scar in the infra-mammary fold and is referred to as the "lollipop" scar. In the 1990's a minimal scar technique developed by a French plastic surgeon named Binelli was popularized to correct breast sagging as a primary mastopexy or in conjunction with a breast implant. This approach did not use large skin reductions, as in previous techniques, but limited scars to the peri-areolar border and used internal sutures to shape the breast gland. A plastic surgeon in South America, Goes, was even more innovative and added the use of synthetic permanent mesh fabrics, placed between the skin and breast gland, to shape the breast in a manner consistent with an internal bra. Because these permanent implants were too frequently palpable or resulted in complications related to the mesh (infection, erosion, chronic pain) most American doctors did not adopt these imaginative techniques.

In recent years, tissue grafts were used to treat these problems. In situations where breast implants or mastectomy surgery had broken down the natural support structures of the lateral, inferior or medial boundaries, a cadaver or animal skin graft, known as acellular dermis, was used to repair the stretched out tissues. In 2010, as an alternative to tissue grafts, Novus Scientific introduced the first long term absorbable synthetic matrix for repair and support of weak or damaged body tissues. Since, three other large medical manufacturers have introduced similar products. But still they all have been used as substitutes for tissue grafts (that are two dimensional sheets) like their acellular dermal predicates.

U.S. Pat. No. 6,055,989 to Rehnke deals with the principle of fascial clefts. Fascial clefts are potential anatomic spaces between layers of known fascia in the body which are fused together at anatomic boundaries. Because the fascia is thin and transparent, like Saran wrap, it can be invisible to those not skilled in the art. However, once one is aware of its presence, its effects can be appreciated and used to great surgical advantage. In the region of the breast, knowledge of the superficial and deep fascial relationships is crucial to all surgeries on this organ. The '989 patent teaches the use of blunt, balloon dissection of the fascial cleft below the breast known as the "sub-glandular space." It was found that the sub-glandular fascial cleft could be opened by balloon dissectors, which would dissect until they reached the peripheral borders of the breast, as defined by the circum-mammary ligament.

The breast is an organ of ectodermal origin, whose cells penetrate the mesoderm and organize into a network of lobular milk producing cells which are connected to the nipple through milk ducts, lined by ductal cells. These breast tissue cells, of ectodermal origin, are surrounded by mesenchymal fat cells, and contained within a dense connective tissue capsule making up what is known as the "corpus mammae". (The corpus mammae is what must be removed during mastectomy for breast cancer.) The corpus mammae is sandwiched between the two layers of superficial fascia and a surrounding insulating layer of fat. Deep to this sandwich, and just on top of the deep fascia of the pectoralis major is the fascial cleft known as the sub-glandular space. The two layers of superficial fascia, that surround the breast, fuse to each other and the deep fascia in a circle around the breast, defining its boundaries and shaping its form; it is known as the "circum-mammary, or circum-mammary or circumferential mammary ligament" The decusating and intermingling fibers of the superficial fascia and deep fascia fibers are mixed with varying amounts of fat, depending on the percent body fat of the patient and the particular aspect of the circum-mammary ligament. For instance, it is thickest and most defined at the inferior border at the fifth costal interspace, or "infra-mammary fold". The medial aspect of this lazy circular border is the reason for the cleavage point between the breast, and is well defined but not thick and fatty. The lateral aspect is less well defined but wide, much more elastic than the inferior or medial boundaries, and located just anterior to the anterior axillary line. Superiorly, the circum-mammary ligament is at its thinnest and hardest to appreciate, in comparison to the infra-clavicular region.

US Published Patent Application No. 2008/0300681 to Rigott et al indicates that if a tissue expander device is placed within layers of tissue in the human anatomy and gradually exerts tensile stress on the tissue, it will induce biologic tissue growth in a desired fashion. Furthermore, it teaches the injection of fat, stem cells (and other progenitor cell) growth factors and pharmaceuticals into the tissue layer experiencing tensile stress. It recapitulates the teachings of the Rehnke '989 patent in regards to the fascial cleft anatomy of the breast and its natural boundary, the circumferential mammary ligament. Rigott states that, "it has been found that these defined layers also offer a region for tissue growth as disclosed herein".

U.S. Published Patent Application No. 2012/0221105 to Altman et al relates to an implantable device for use in tissue and ligament repair. The device is comprised of knitted, slowly absorbable silk fibers with a continuous fiber traversing it. The preferred embodiment involves its use as a sheet of fabric, or mesh, that is used in place of acellular dermal cadaver grafts in the performance of breast reconstructions and all manner of cosmetic breast surgeries and mention that a scaffold can be used, as an internal scaffold to act as a bra to immediately support a geometrically complex implantation site at the time of surgery which would ideally provide the body both time and structure necessary for optimal healing. Simple sheets of two dimensional matrix are used to reinforce various regions of the breast depending on the need of each clinical case. The device, shown as a sheet of fabric, is simply folded over to reinforce regions of the breast borders, such as infra-mammary fold, medial cleavage, or lateral border. Known surgical procedures and maneuvers that have been a part of plastic surgery of the breast for ten years are used with the substitution of the absorbable silk synthetic material for the traditional acellular dermis product.

U.S. Pat. No. 7,998,152 B2 to Frank shows an implantable device made for use in a peri-areolar mastopexy, which allows for a transfer of shaping tensions to the device, as opposed to simply on to the permanent purse string used in per-areolar mastopexy. The device is annular or frusto-conical in configuration and can be constructed of absorbable material or acellular tissue graft. The truncated, cone shaped device may have a series of teeth extending out from the surface that engages the breast gland, and thus holds it in the more desirable projecting state seen in youthful breasts. It is designed to be placed through the peri-areolar incision, under the skin and on the superficial surface of the breast gland. It allows for use of an absorbable peri-areolar suture, that tightens the skin envelop around the areola. The device addresses only the skin envelope relaxation, seen in breast ptosis; it does not address the more important causation of breast sagging, the enlargement and stretching out of the circum-mammary ligament.

Professors Jain Farhadi and Kefah Mokbel have performed a surgical procedure at Guy's Hospital in London, making use of an implantable device developed in 2007, wherein a synthetic bra made of a silicone cup is placed between the skin and the lower pole of the breast; it is anchored to the rib cage with silk straps.

SUMMARY OF THE INVENTION

The present invention overcomes the above described disadvantages of the prior art by preventing breast sagging, or ptosis, which comes from the stretching out of the superficial fascial system (circum-mammary ligament or CML) that shapes and conforms the breast to its natural position on the chest wall. The breast itself has no shape apart from the superficial fascia system. The CML establishes the position on the chest wall and pushes the volume of the breast into a projecting vector as the diameter of this ring of fascia gets smaller. The anterior and posterior lamella of the superficial fascia control the projection and thus shape the breast. Ptosis is a result of both the diameter of the CML enlarging, and the anterior/posterior lamella of the superficial fascia relaxing. The loss of support allows the skin of the breast to stretch as a result. Factors such as genetic inheritance (strength of skin and connective tissue), amount of body fat, history of weight gain and loss, number of pregnancies, breast feeding, and shape and contour of the chest wall, are the contributing factors that determine a woman's natural breast shape. The typical order of things is that women develop breasts at puberty and are "perky", followed by enlarged breast volume during child bearing years, at which time they develop a pleasant tear drop fullness; they involute or deflate after child bearing, at which time they then sag or, in medical terms, become ptotic. In the modern, era woman have resisted this natural order of things (the "National Geographic" condition of the breast). Many modern women have sought help through plastic surgery, taking advantage of breast reduction, breast lifts and/or breast implants to correct these changes and preserve a more youthful breast.

The present invention is a device in the form of an internal brassiere, made of long term, absorbable materials. It is three dimensionally shaped to mimic the breasts own fascial system of support, the circum-mammary ligament (CML). The device is circular at its base on the chest wall, which is placed on top of the deep fascia of the pectoralis major. It has various thicknesses and densities, with some components being a two dimensional sheet with low weight density, composed entirely of absorbable material. Other components have a three dimensional shape with a higher weight density and have a small percentage of permanent, non-absorbable material.

The first component of the device of the present invention is a circular, three dimensional tube or ring-like member that has a heavier weight density, and has a portion of the fibers comprised of a non-absorbable material, such as polypropylene. A non-absorbable suture is located within the tube. It can be inserted in a large diameter condition and, once anchored to the CML, cinched into a smaller diameter by pulling its internal suture tight and tying it. It has a pleated, gathered nature, like an accordion, which allows it to have a variable diameter. It is designed to be placed in the plane of the deep fascia of the pectoralis muscle, just within the circum-mammary ligament. Once the device is positioned, the surgeon sutures the circular tube to the circum-mammary ligament. This is accomplished with interrupted, non-absorbable sutures that are placed along the entire lateral portion of the CML, as well as the entire infra-mammary fold portion of the CML, and the lower ⅔ of the medial portion of the CML. Superiorly, the device leaves its close association with the circum-mammary ligament and continues in its circular path, across the deep pectoral fascia, to rejoin the lateral portion of the CML. It is anchored to the superior deep fascia with a running suture.

In another embodiment, there is no permanent suture within the first or tube member. It is attached to the circum-mammary ligament with a non-absorbable running suture that courses in and out of the ligament and first member ring, in such a fashion as to pull both the CML and first member ring into a smaller diameter when the suture is pulled taut and tied.

The second member of the device is a tarpaulin-like sheet, that is a two dimensional sheet of low weight, completely long term absorbable matrix. It is fixed to the interior of the first purse string member in a way as to allow the first member to cinch down to a smaller diameter that matches the diameter of the second member (or the desired new diameter of the CML).

The third member resembles the "cup" of a traditional bra, with a radius matching the desired size of the enhanced breast, and is attached, with non-absorbable sutures, to the first tubular member after it is secured and tightened. It is three dimensional with a thickness of roughly 8 to 10 millimeters. This thickness tapers to 1 to 2 mm. at the periphery of the cup. The cup can be complete coverage in its anterior-superior breast dimension, or it can have a half, or demi cup, coverage in some embodiments. Finally, it has the lowest weight density of fibers and greatest open space interstices between these fibers. The fibers can be woven, knitted, or loosely arranged like a felt. This member is designed as a fully, long term absorbable component in some embodiments, but can contain a small percentage of non-absorbable fibers in other embodiments. It is a three dimensional matrix which allows for arterial and tissue ingrowth, as is commonly seen in existing two dimensional long term absorbable matrices; it can be used to engineer a thicker sub-cutaneous fat layer when autologous fat transplantation is injected into its interstices, as part of a delayed procedure performed at a later date. This attribute of the internal bra provides a better soft tissue coverage when an implant is indicated, and avoids the necessity of sub-muscular implant placement, which weakens the foundation of the circum-mammary ligament. In some applications, an implant can be completely avoided by the narrowing of the CML foot print on the chest wall, which gathers the breast tissue and projects it. The third member cup can be used for small to medium autologous augmentation purposes when fat is transferred to the engineered third member.

The full cup embodiment travels up to the upper pole of the breast, tapering off to a 1-2 mm thickness at its upper edge. In this case the anterior cup is the same diameter as the second member tarpaulin. In the "demi-cup" version, the upper anterior edge of the cup parallels the inferior-lateral edge of the Pectoralis Major, and can be sewn to it when sub-muscular implant placement is indicated.

In another embodiment, the three dimensional cup, third member, can have surface coatings of growth factors, plasma rich platelet gel, or stem cells loaded to its surface at implantation.

Accordingly, the present invention creates a long term absorbable matrix which is shaped into an internal bra device, whose shape and engineering is dictated by the breast's natural superficial fascial anatomy—the circum-mammary ligament. It recognizes that a major contributor to breast ptosis is the stretching out of this circum-mammary ligament when a heavy breast or breast implant slides down off the inclined chest wall, while a person is in a supine or prone position. The design of the device makes use of three members which assembled together form the internal bra. The first, and most important, is a circular tube with an internal purse string, which is designed to be placed in the sub-glandular plane adjacent the peripheral CML. It is anchored to the circular ligament with permanent interrupted sutures.

When the purse string is pulled tight and tied, the base foot print of the breast is narrowed and thus gathers the breast together and adds to its projection. The tarpaulin second member is thin and virtually a two dimensional sheet, that adds to the anchorage of the device to the chest wall. The third, cup-like, member is located anteriorly and is placed deep to skin and sub-cutaneous fat layer and superficial to the breast gland in mastopexy procedures. When a breast implant is called for, the anterior cup is placed behind the skin, sub-Q fat and breast gland, but superficial to the breast implant. It adds to the soft tissue coverage of the implant by engineering a fat layer when autologous fat transfer is performed into the 8-10 mm thick cup. This is especially important in reconstructive cases, where the breast gland has been removed and the soft tissue overlying the implant is thin.

It should be appreciated that the present invention is particularly advantageous for women who have had plastic surgical enhancement of the breast (with breast implants or fat grafting), mastopexy, breast reduction, or immediate breast reconstruction following mastectomy for breast cancer. Additionally, the internal bra of the present invention provides effective support and shaping for women with breast implants. The internal, long term absorbable matrix brassiere according to the present invention provides a synthetic internal brassiere that mimics the principal structure of nature's superficial fascial bra, the circum-mammary ligament.

The present invention additionally provides a pre-fabricated internal bra, designed for surgical use, to prevent the relaxation of the fascial shaping structures of the breast that hold it and, when applicable, also hold breast implants in their useful position on the chest.

Another feature of the present invention is that an improved pre-fabricated long term absorbable matrix device according to the present invention is designed for surgical creation of an internal bra that mimics and strengthens the circum-mammary ligament.

The previously mentioned prior art devices do not describe a pre-fabricated internal bra, designed for surgical use, to prevent the relaxation of the fascial shaping structures of the breast that hold it, and when applicable also hold breast implants, in their youthful position on the chest. Therefore, it can be appreciated that there exists a continuing need for a new and improved pre-fabricated long term absorbable matrix device, designed for surgical creation of an internal bra that mimics and strengthens the circum-mammary ligament.

Other aspects and advantages of the present invention will become apparent from the following description of the invention taken in conjunction with the accompanying drawings wherein like parts in each of the several figures are identified by the same reference characters.

DETAILED DESCRIPTION OF THE INVENTION

Figure 6:
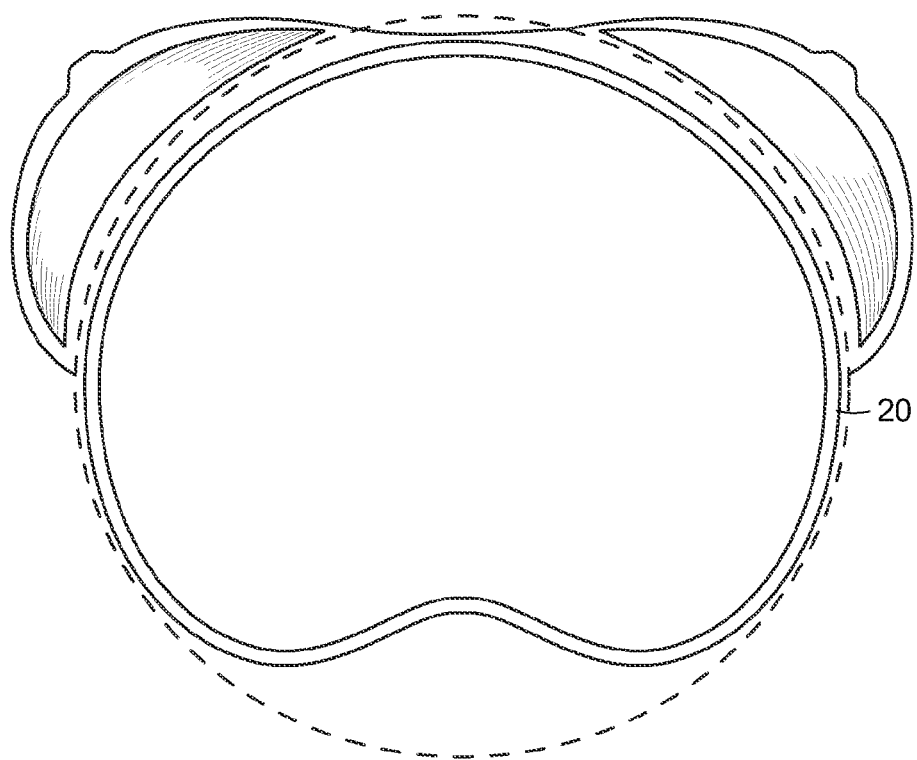
Figure 7:
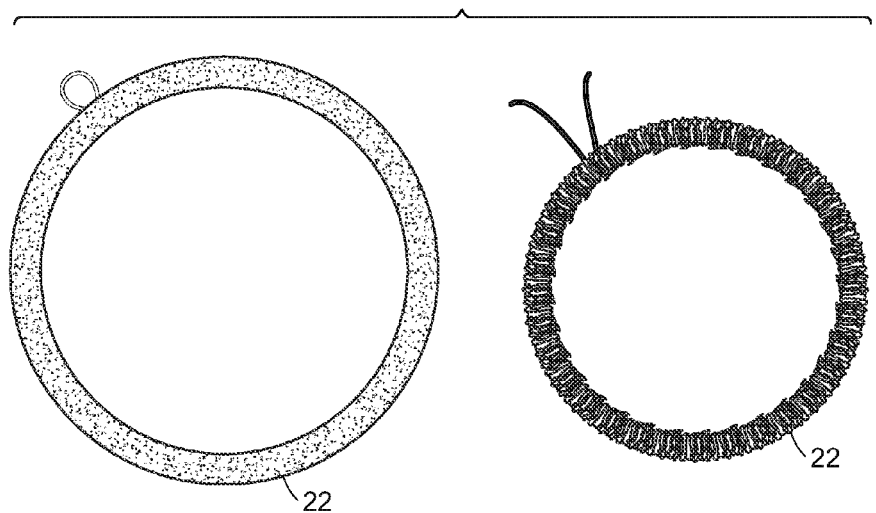
FIG. 7 shows plan views of a circular tube member of the internal bra according to the present invention.

The problem that exists when a woman with sizable breasts sleeps in a recumbent horizontal position is illustrated in FIG. 6.

Figure 1A:
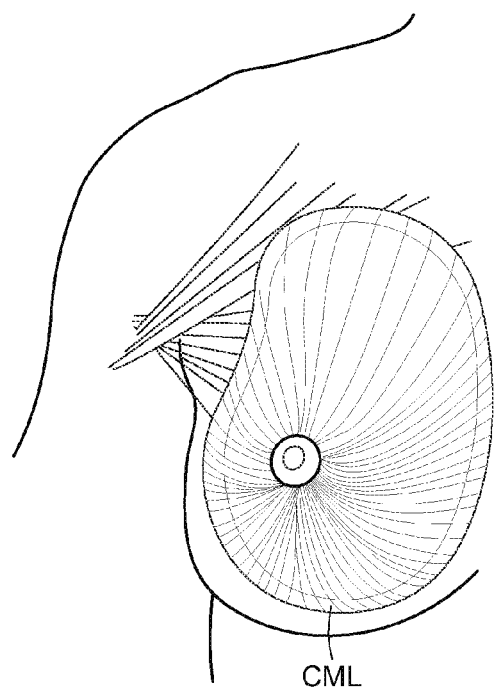
FIGS. 1A and 1B show the circum-mammary ligament surrounding the breast and being weaker laterally, FIG. 1B including an enlarged sectional portion of the breast.
Figure 1B:
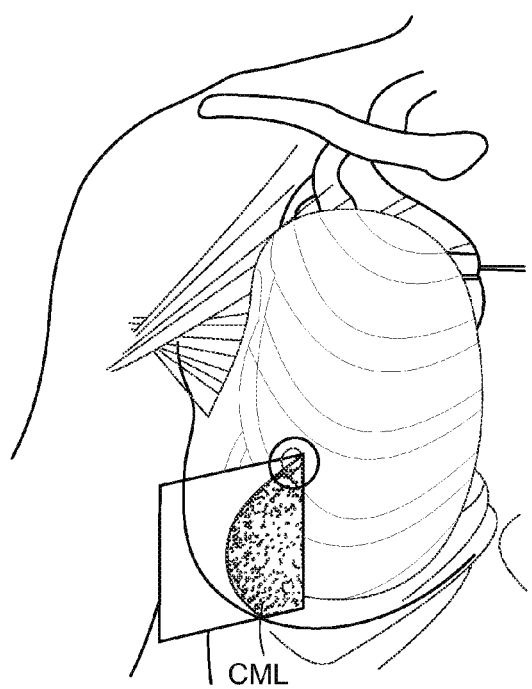
Figure 2:
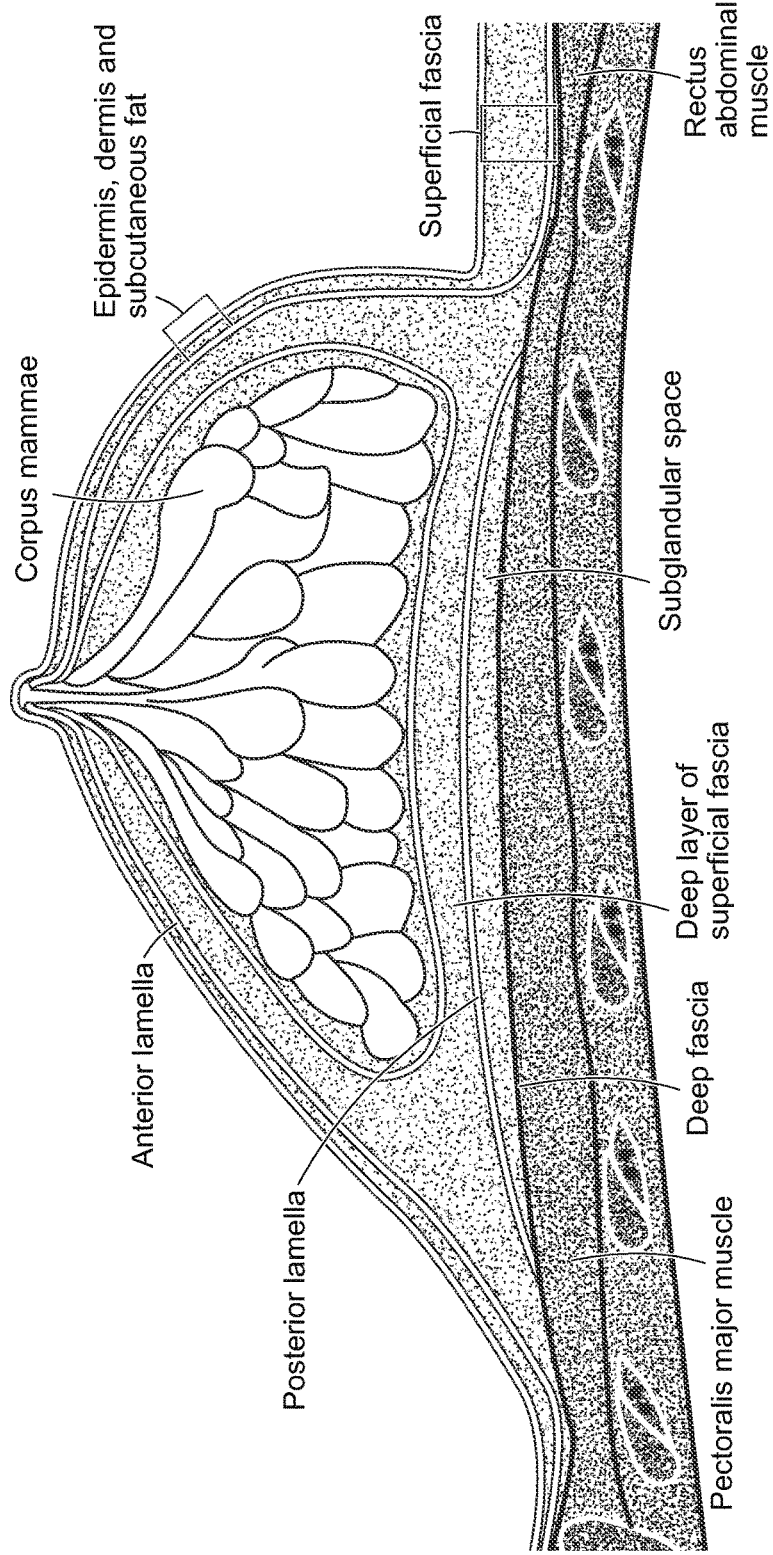
FIG. 2 is a sectional sagital view of the superficial fascia system of the breast.
Figure 3:
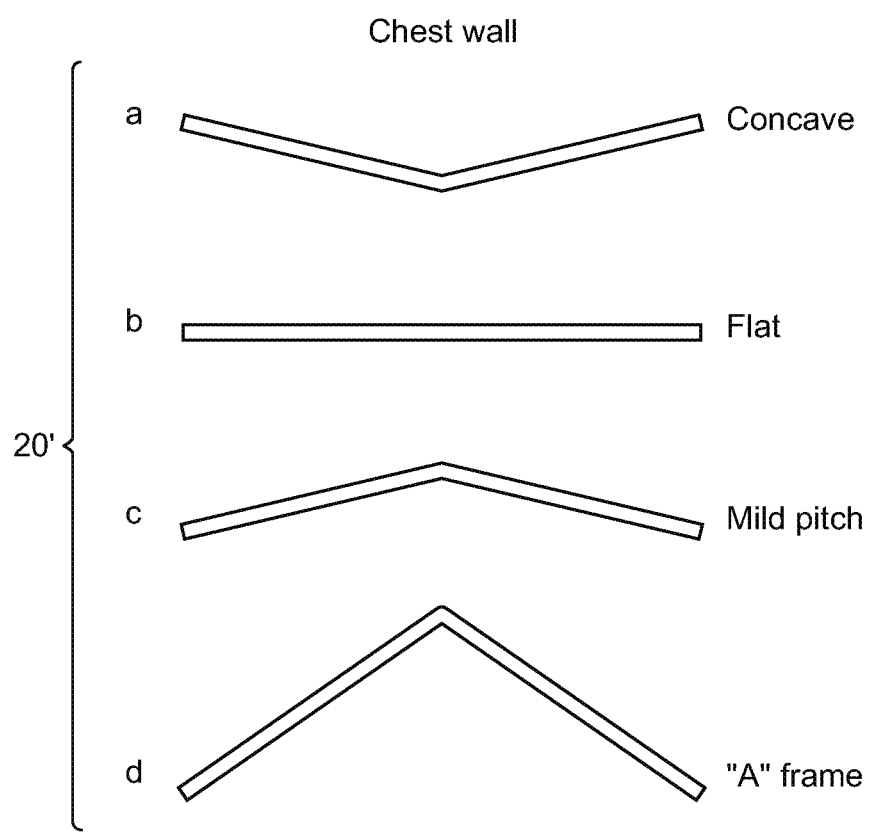
FIG. 3 shows the various slopes in the human chest wall with a person in the supine position and illustrates the great deal of variation seen in the "topography" of the chest wall from one person to another, and from side to side in the same person, and also illustrates that asymmetry in human anatomy is the rule, not the exception such that a person could have a flat right side of the chest, and a sloped pitch to the left side.
Figure 4:
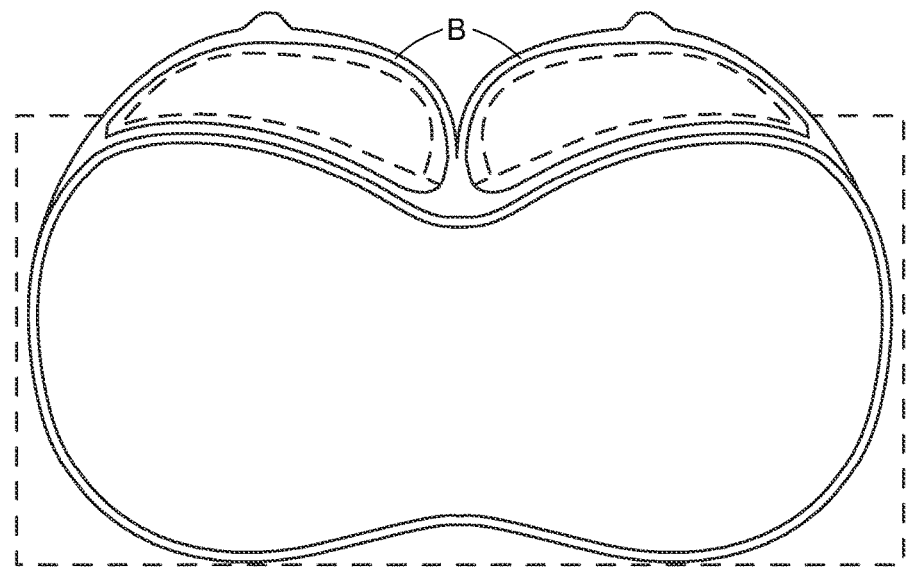
FIGS. 4, 5 and 6 illustrate a sunken central chest, or pectus excavatum, a rectangular shape chest, or flat chest, which gives the best support for the breast and implants when present and when the pitch of the chest wall begins to progressively become more sloped, and lateral movement of the breast, respectively.
Figure 5:
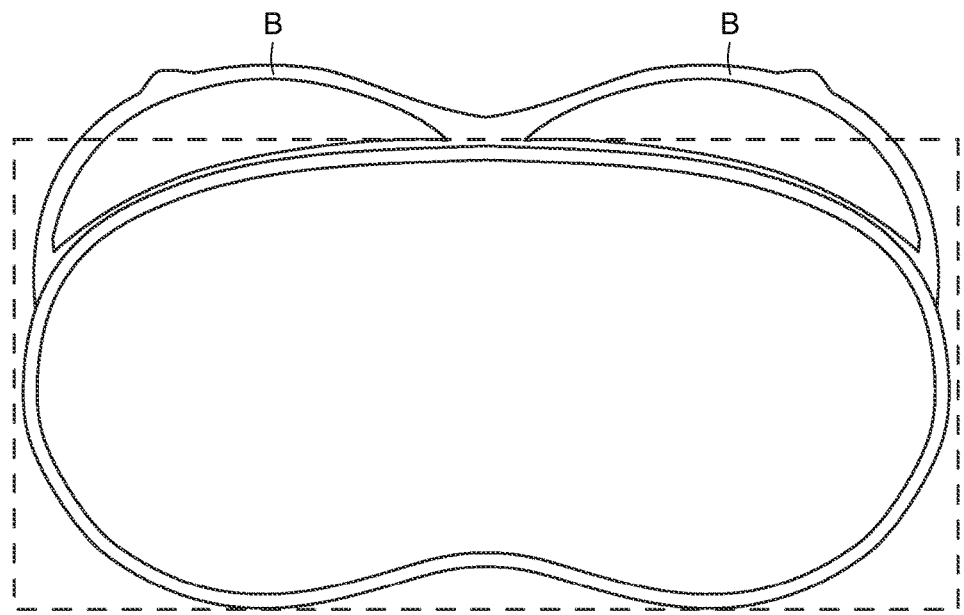

The chest wall 20 generally slopes downward as one moves from the center, or sternal area, towards the lateral chest wall. The various configurations exist as a result of the basic patterns 20' seen in FIG. 3 and the fact that there is a propensity for asymmetry in the human body, largely because of asymmetry of the underlying skeleton. The breast B tends to follow the contour of the chest wall, with unusually close cleavage in conditions like those seen in FIG. 4. This condition is known as pectus excavatum. The chest configuration that is most desirable for maintaining youthful perky breast, or keeping a desirable position of the breast following plastic surgery, is the rectangular shape seen in FIG. 5. In this situation there exists a stable, horizontal support for the mass of the breast, with or without a breast implant. During the roughly 8 hours per day that a person sleeps they are in either the supine or prone position at least half of the time. This rectangular configuration protects the circum-mammary ligament from stretching out by supporting the breast in the horizontal position. The worst condition of the chest for maintaining a youthful, perky breast is that seen in FIG. 6—the round or cylindrical chest 20. In this state, the breasts are basically cantilevered off of the chest wall without any support.

Figure 8:
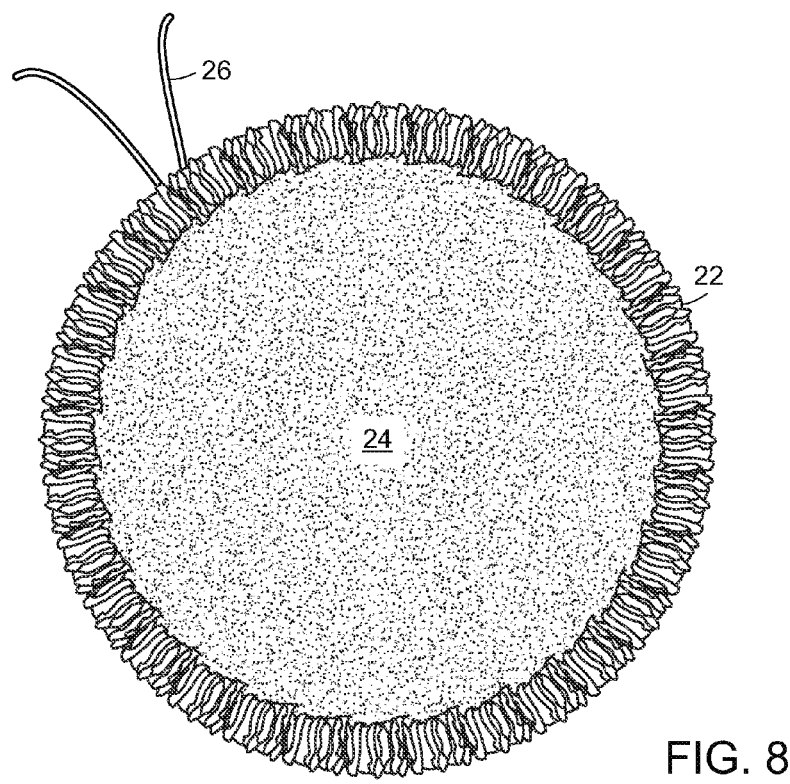
FIG. 8 is a plan view of the circular member shown in FIG. 7 cinched with draw suture tied and a central tarpaulin in place.
Figure 9B:
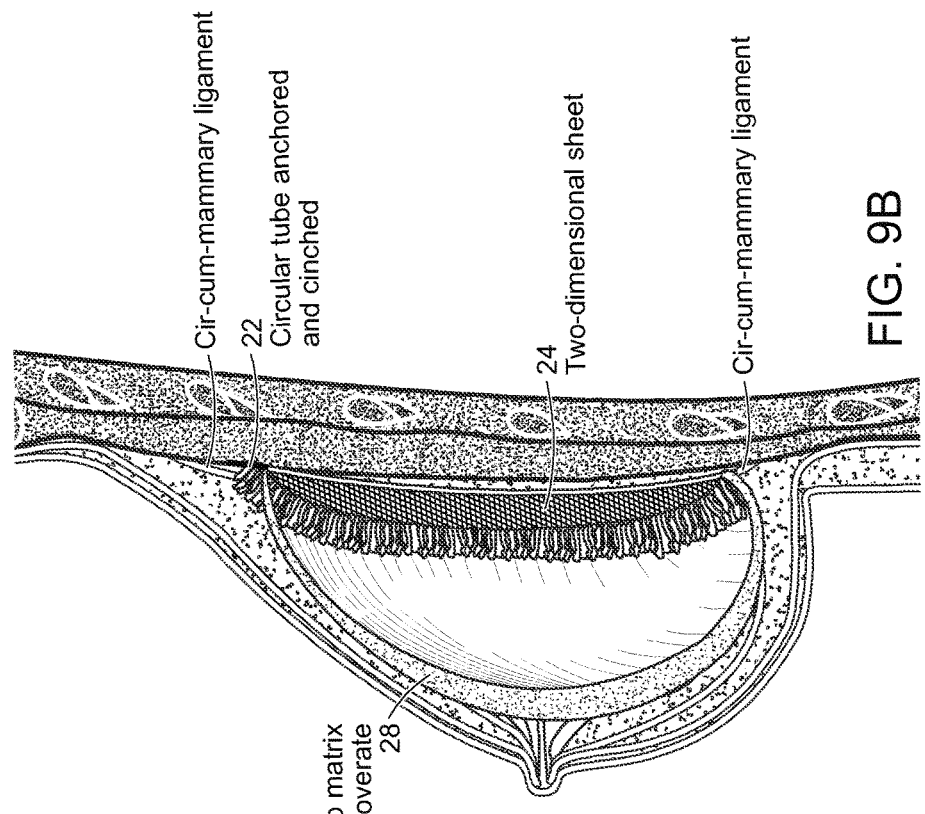
FIG. 9B shows the internal bra fully assembled with a full cup.
Figure 9A:
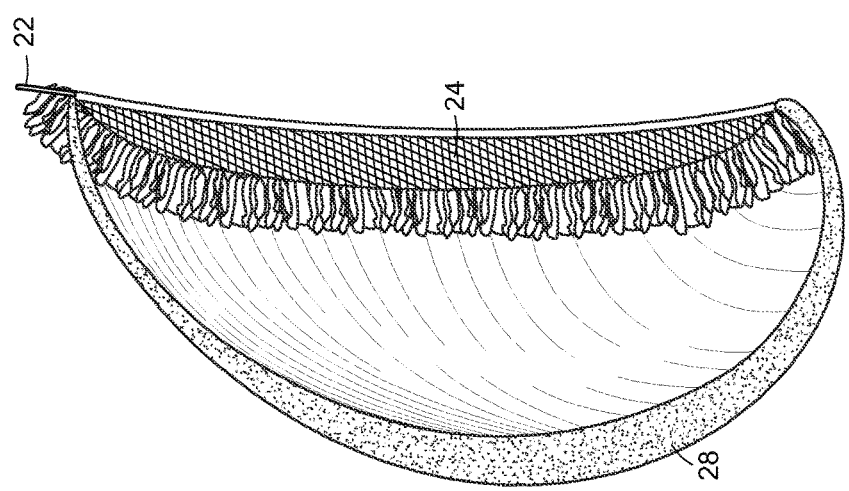
FIG. 9A is a side view of a third member of the internal bra of the present invention showing a cup assembled to the members shown in FIGS. 7 and 8.
Figure 10B:
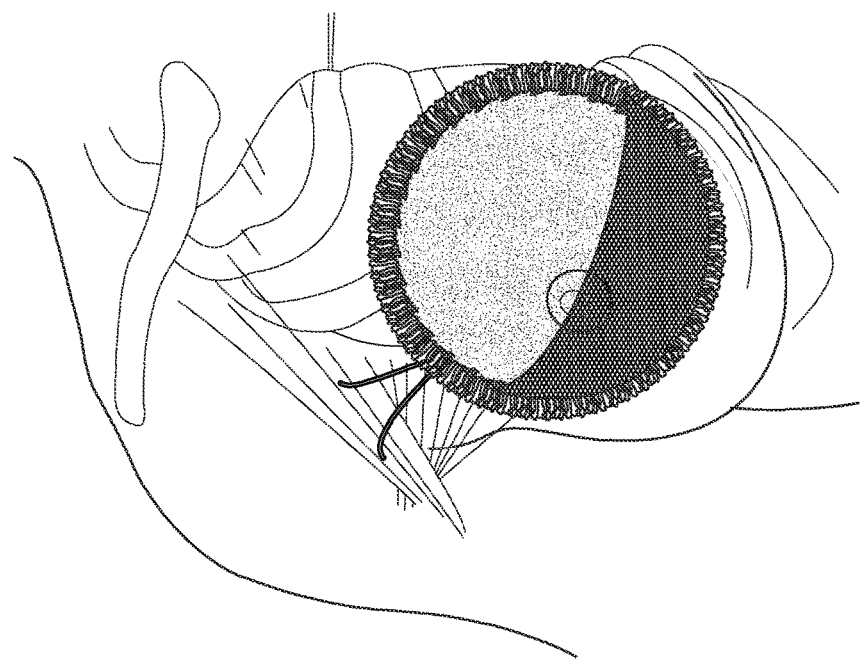
FIGS. 10A and 10B show assembly of the internal bra of the present invention with a demi cup.
Figure 10A:
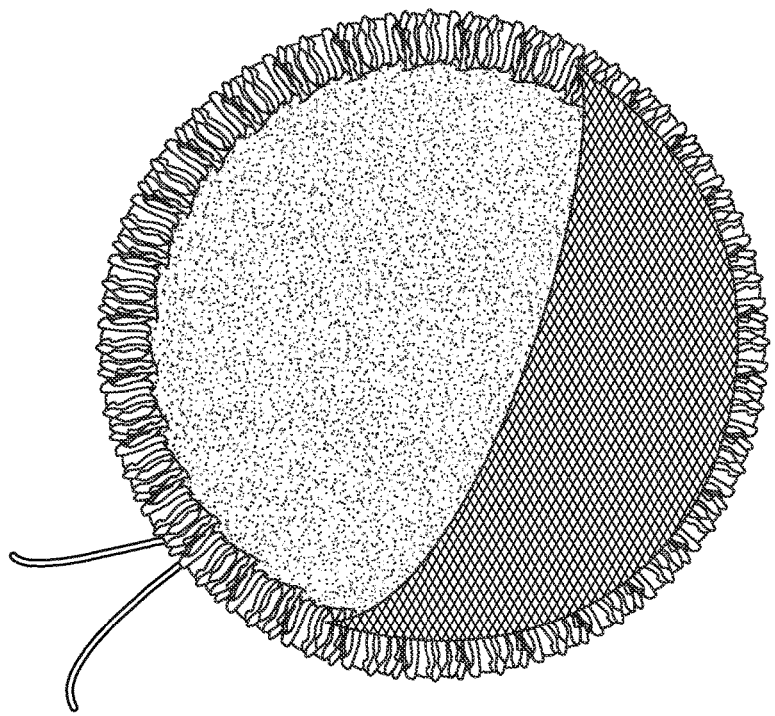

In order to prevent the breast from "rolling down hill" in the recumbent position during sleep, the present invention is utilized as described in FIGS. 7-11. The device is used when weakening and stretching out of the circum-mammary ligament exists; or due to high risk anatomy (like a severe pitch to the slope of the chest wall with weak connective tissue) posing the high chance of sagging after plastic surgery. The first and second members, 22 and 24, of the device are placed into the surgical pocket, behind the breast gland and on top of the pectoral muscle, then anchored to the surrounding CML with non-absorbable suture 26. The device is cinched to the desirable smaller diameter, thus tightening the CML and gathering the breast together in a higher, more projecting position on the chest (FIG. 8). When desired, a third three dimensional cup (with internal radius and measuring roughly one centimeter at its thickest central portion) is positioned behind the breast in an augmentation but in front of the implant, then fixed in place with sutures to the inferior portion of the first member. In larger breasted woman, who are undergoing a reduction or lift, the third member is placed below the anterior lamella of superficial fascia and in front of the corpus mammae. In breast reconstruction using a skin, nipple, and CML sparing technique, the cup 28 is place below the anterior lamella and in front of the breast implant. The third member adds strength and support to the skin superficial fascia component of breast as the patient's fibroblast and blood vessels grow into and replace the slowly dissolving matrix. It also can serve as a platform for autologous fat transplantation, in situations where soft tissue coverage is insufficient or when an implant is not desired.

Figure 11:
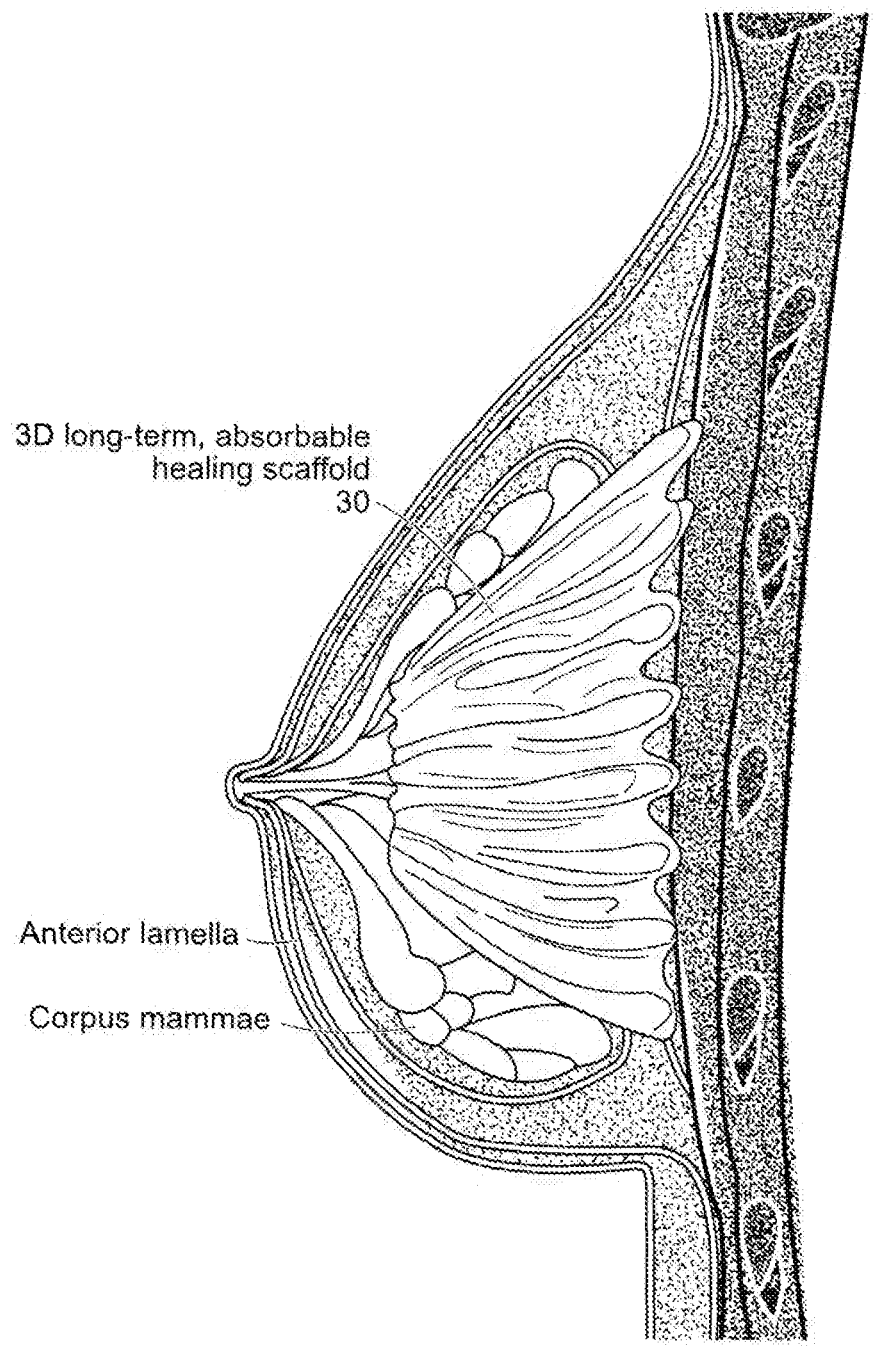
FIG. 11 shows a modification of the internal bra of the present invention utilizing a long term absorbable healing scaffold with pleats.

In the embodiment shown in FIG. 11, a three dimensional pleated pyramidal structure 30 replaces the "cup" and "tarpaulin" members, and is anchored with sutures within the circular tube structure. Its thickness at the periphery is roughly 8-10 mm and increases in thickness up to 3-4 cm at the apex of the pyramid. It is of the very "low weight" or low density variety and serves as a sponge that autologous fat can be transplanted into and for a support of the nipple/breast projection.

Some materials that can be used for the long term absorbable matrix (or mesh) include Novus Scientific TIGR mesh, Allergen Seri Surgical Scaffold; Tepha, Inc. owns a polymer (Poly-4 Hydroxybutyrate) that they license to Bard under the name Phasix, and to Galatea under the name GalaFLEX; Gore long term absorbable mesh called Bio A, and Ethicon Ultrapro.

The device of the present invention prevents the breast (and breast implants when present) from pushing down and weakening natures internal support—the circum-mammary ligament. Change in the shape of the breast is due to gradual nightly erosion of the ligament over time, in the same way that orthodontia can move teeth through the jawbone with continuous directional pressure. This slowly absorbable, synthetic device, with its three members of varying density and thickness, are positioned and assembled during surgery to correct and strengthen the superficial fascia system that defines breast shape—thus constituting an internal long-term absorbable bra.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An internal, long term absorbable matrix brassiere comprising
   a circular tube member adapted to be internally fixed to the chest of a woman; and
   a cup held within said tube member, said cup being formed of a pleated, long term absorbable material forming a scaffold.

2. An internal, long term absorbable matrix brassiere as recited in claim 1 and further comprising a suture disposed within said tube member to be anchored to the circum-mammary ligament, said suture having a pleated, gathered nature to have a smaller diameter upon being cinched by pulling and tying said suture.

3. An internal, long term absorbable matrix brassiere as recited in claim 1 and further comprising a running suture that courses in and out of said tube member and the circum-mammary ligament to pull said tube member and the circum-mammary ligament into a smaller diameter when said running suture is pulled taut and tied.

4. An internal, long term absorbable matrix brassiere as recited in claim 1 wherein said cup is made of a three-dimensional matrix, primarily of long term absorbable fibers allowing for arterial and tissue ingrowth.

5. An internal, long term absorbable matrix brassiere as recited in claim 1 wherein said cup is a three-dimensional pleated pyramidal-type structure anchored within said tube member with sutures.

6. An internal, long term absorbable matrix brassiere as recited in claim 5 wherein said cup has a periphery and an apex and said pleated material has a thickness at said periphery less than the thickness at said apex.

* * * * *